(12) United States Patent
Fujimori

(10) Patent No.: US 8,348,835 B2
(45) Date of Patent: Jan. 8, 2013

(54) CAPSULE TYPE ENDOSCOPE

(75) Inventor: Noriyuki Fujimori, Tokyo (JP)

(73) Assignee: Olympus Corporation, Tokyo (JP)

( * ) Notice: Subject to any disclaimer, the term of this patent is extended or adjusted under 35 U.S.C. 154(b) by 1503 days.

(21) Appl. No.: 11/492,603

(22) Filed: Jul. 25, 2006

(65) Prior Publication Data

US 2006/0264083 A1 Nov. 23, 2006

Related U.S. Application Data

(63) Continuation of application No. PCT/JP2005/000869, filed on Jan. 24, 2005.

(30) Foreign Application Priority Data

Jan. 26, 2004 (JP) ................................. 2004-017137

(51) Int. Cl.
*A61B 1/06* (2006.01)
(52) U.S. Cl. ........................................................ 600/160
(58) Field of Classification Search .................. 600/109, 600/117, 118, 160
See application file for complete search history.

(56) References Cited

U.S. PATENT DOCUMENTS

| | | | | | |
|---|---|---|---|---|---|
| 6,836,377 | B1 * | 12/2004 | Kislev et al. | ................. | 359/708 |
| 2002/0109774 | A1 * | 8/2002 | Meron et al. | ................. | 348/74 |
| 2003/0028078 | A1 * | 2/2003 | Glukhovsky | ................. | 600/109 |
| 2003/0117491 | A1 * | 6/2003 | Avni et al. | ................. | 348/77 |
| 2003/0158503 | A1 * | 8/2003 | Matsumoto | ................. | 600/593 |
| 2003/0171648 | A1 * | 9/2003 | Yokoi et al. | ................. | 600/109 |
| 2003/0171649 | A1 * | 9/2003 | Yokoi et al. | ................. | 600/109 |
| 2003/0171652 | A1 * | 9/2003 | Yokoi et al. | ................. | 600/160 |
| 2003/0171653 | A1 * | 9/2003 | Yokoi et al. | ................. | 600/160 |
| 2003/0227547 | A1 * | 12/2003 | Iddan | ................. | 348/151 |
| 2004/0027459 | A1 * | 2/2004 | Segawa et al. | ........... | 348/207.99 |
| 2004/0171914 | A1 * | 9/2004 | Avni | ................. | 600/160 |
| 2004/0171915 | A1 * | 9/2004 | Glukhovsky et al. | ......... | 600/160 |
| 2006/0189844 | A1 * | 8/2006 | Tien | ................. | 600/143 |

FOREIGN PATENT DOCUMENTS

| | | |
|---|---|---|
| EP | 1 342 447 A2 | 9/2003 |
| JP | 2001-91860 | 4/2001 |
| JP | 2003-325441 | 11/2003 |

* cited by examiner

*Primary Examiner* — Philip R Smith
(74) *Attorney, Agent, or Firm* — Scully Scott Murphy & Presser, PC

(57) ABSTRACT

A capsule-type endoscope includes an illumination board which is prepared to mount an illuminating electronic component necessary to illuminate a test region of a test subject with illumination light; an image sensor which has a light-receiving surface including an effective area and an ineffective area, the illumination light reflected from the test region being received to generate an image of the test region in the effective area, the ineffective area not contributing to the image generation; an imaging board which is arranged in parallel with the illumination board, the image sensor being mounted on the imaging board; and a component arrangement unit in which the illuminating electronic component is arranged, the illuminating electronic component being provided in an area on the illumination board, the area on the illumination board being obtained by projecting the ineffective area in the light-receiving surface of the image sensor to a direction orthogonal to the light-receiving surface of the image sensor.

4 Claims, 15 Drawing Sheets

CAPSULE TYPE ENDOSCOPE

CROSS-REFERENCE TO RELATED APPLICATIONS

This application is a continuation of PCT international application Ser. No. PCT/JP2005/000869 filed Jan. 24, 2005 which designates the United States, incorporated herein by reference, and which claims the benefit of priority from Japanese Patent Application No. 2004-07137 filed Jan. 26, 2004, incorporated herein by reference.

BACKGROUND OF THE INVENTION

1. Field of the Invention

The present invention relates to a capsule-type endoscope which is introduced into a test subject to observe a test region.

2. Description of the Related Art

In recent years, a capsule-type endoscope has been proposed in the field of an endoscope. The capsule-type endoscope is introduced from a mouth into a body cavity of the test subject. An imaging device in the capsule-type endoscope picks up images of alimentary canals such as the small intestine and the large intestine, whereby the capsule-type endoscope can collect information on the inside of the body cavity. An illumination unit (light emitting diode) and an objective lens are fixed in a front portion of the capsule-type endoscope, whereas a main block to which a circuit board is fixed and an outer casing which houses the main block are provided in a rear portion of the capsule-type endoscope. An image sensor, an electronic component that controls the image sensor, an electronic component for transmission, and a power switch, and the like are fixed to the circuit board, and an antenna board is connected to the circuit board. A battery is incorporated into the circuit board. The outer casing includes a hemispherical transparent cover and a cylindrical cover. A front portion of the main block is covered with the transparent cover, and a rear portion of the main block is covered with the cylindrical cover. A rear-end portion of the cylindrical cover is formed in a hemispherical shape. The circuit board is fixed to the main block, the main block is accommodated in the outer casing, and the capsule-type endoscope is assembled by bonding the transparent cover and the cylindrical cover in a watertight manner (for example, see JP-A (KOKAI) No. 2001-91860).

SUMMARY OF THE INVENTION

A capsule-type endoscope according to one aspect of the present invention includes an illumination board which is prepared to mount an illuminating electronic component necessary to illuminate a test region of a test subject with illumination light; an image sensor which has a light-receiving surface including an effective area and an ineffective area, the illumination light reflected from the test region being received to generate an image of the test region in the effective area, the ineffective area not contributing to the image generation; an imaging board which is arranged in parallel with the illumination board, the image sensor being mounted on the imaging board; and a component arrangement unit in which the illuminating electronic component is arranged, the illuminating electronic component being provided in an area on the illumination board, the area on the illumination board being obtained by projecting the ineffective area in the light-receiving surface of the image sensor to a direction orthogonal to the light-receiving surface of the image sensor.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule-type endoscope according to the present invention will be described in detail with reference to the accompanying drawings. However, the present invention shall not be limited to the embodiments.

Figure 1:
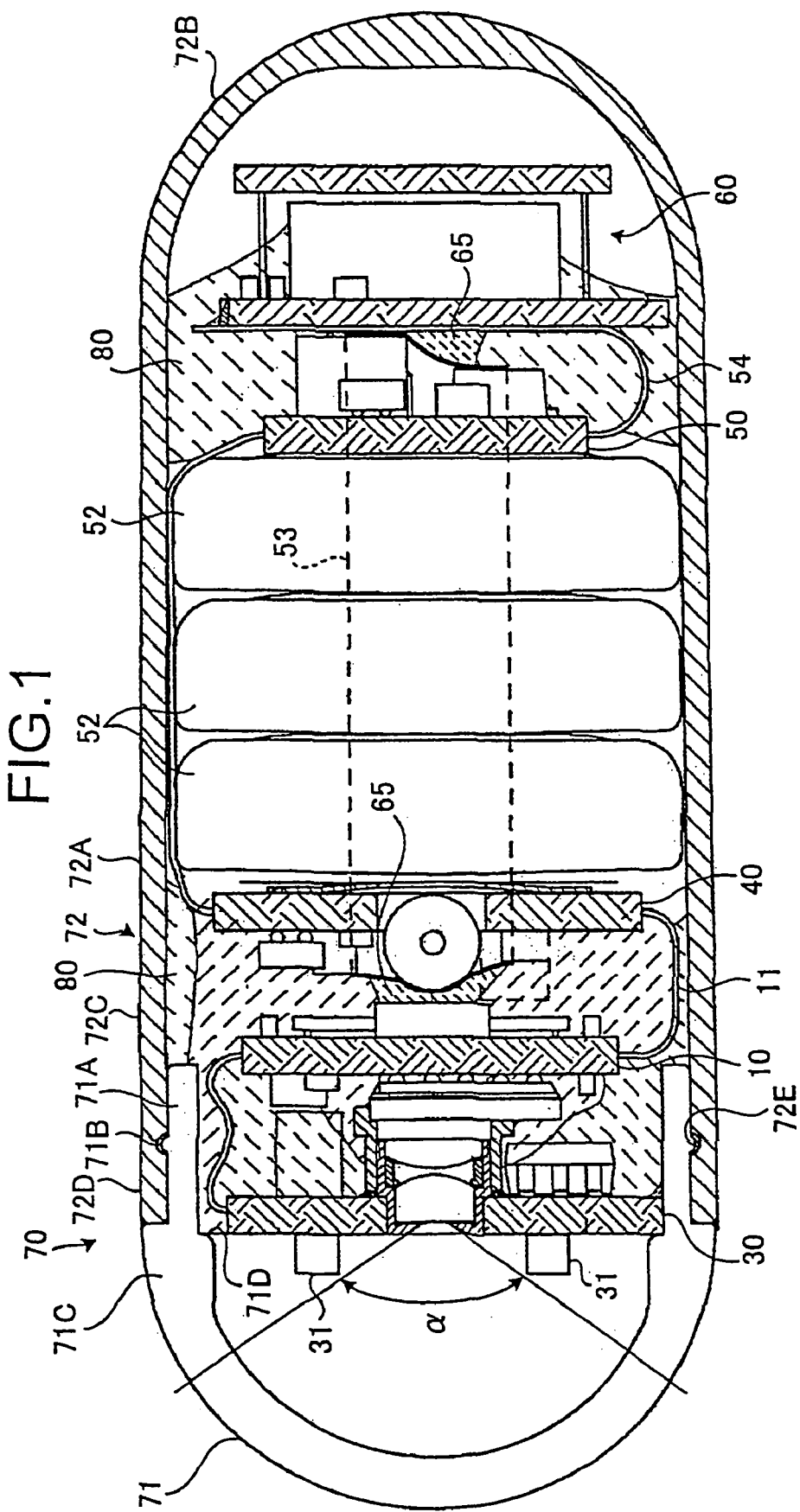
FIG. 1 is a sectional side view showing a configuration of a capsule-type endoscope according to an embodiment of the invention.
Figure 2:
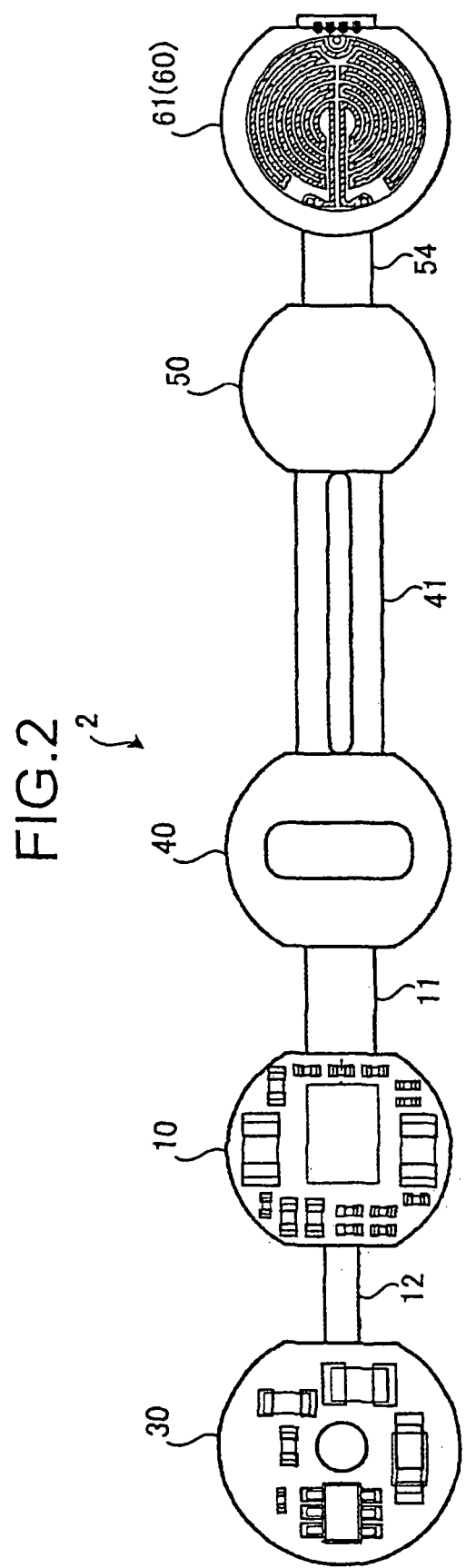
FIG. 2 is a top view showing an unfolded form of a rigid/flexible wiring board shown in FIG. 1.
Figure 3:
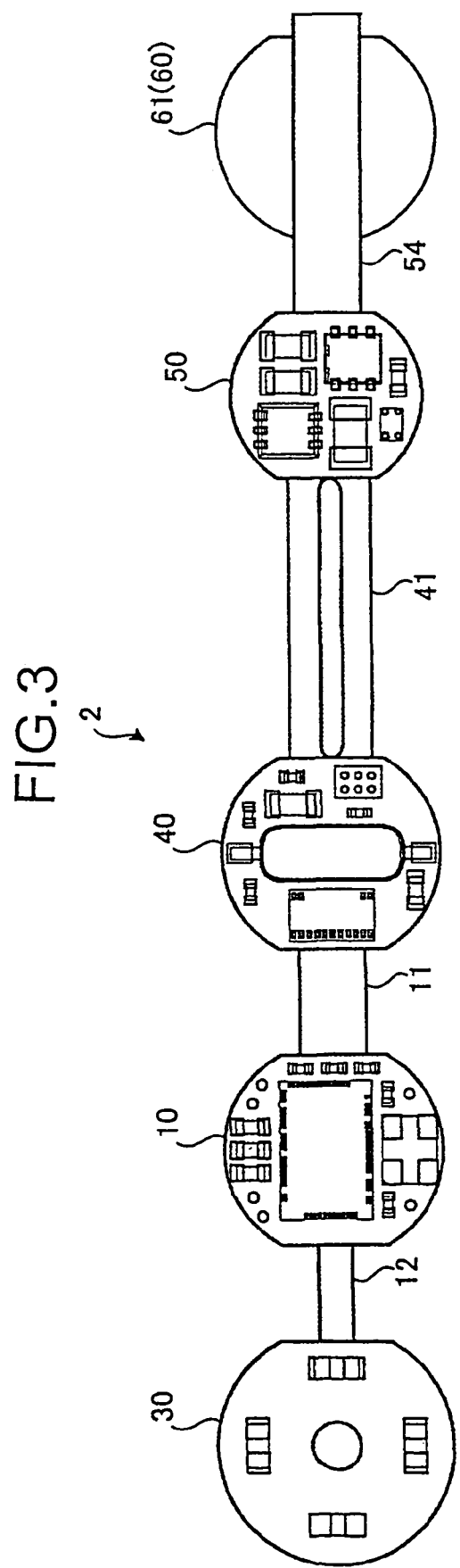
FIG. 3 is a bottom view showing the unfolded form of the rigid/flexible wiring board shown in FIG. 1.
Figure 4:
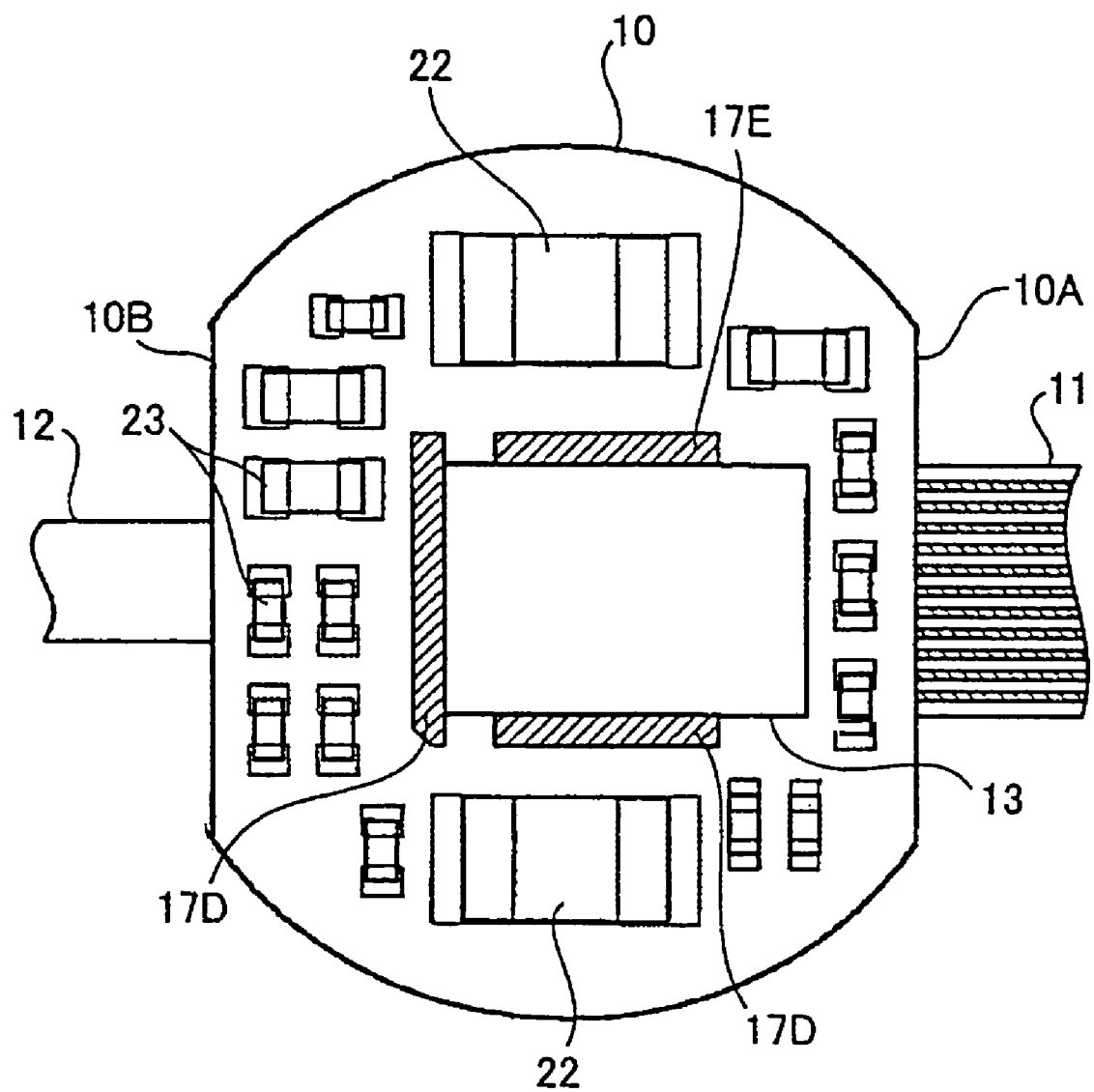
FIG. 4 is a view showing a front surface of an imaging board.
Figure 5:
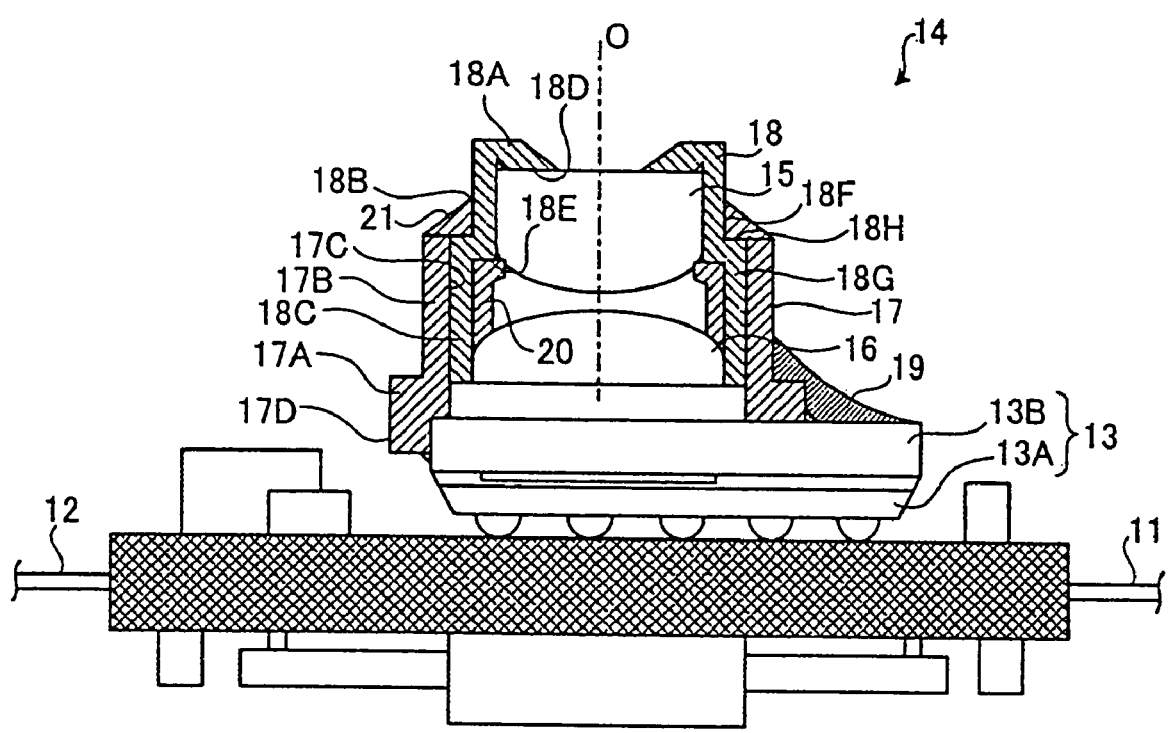
FIG. 5 is a sectional side view showing a state in which a lens attachment member is attached to the imaging board.
Figure 6:
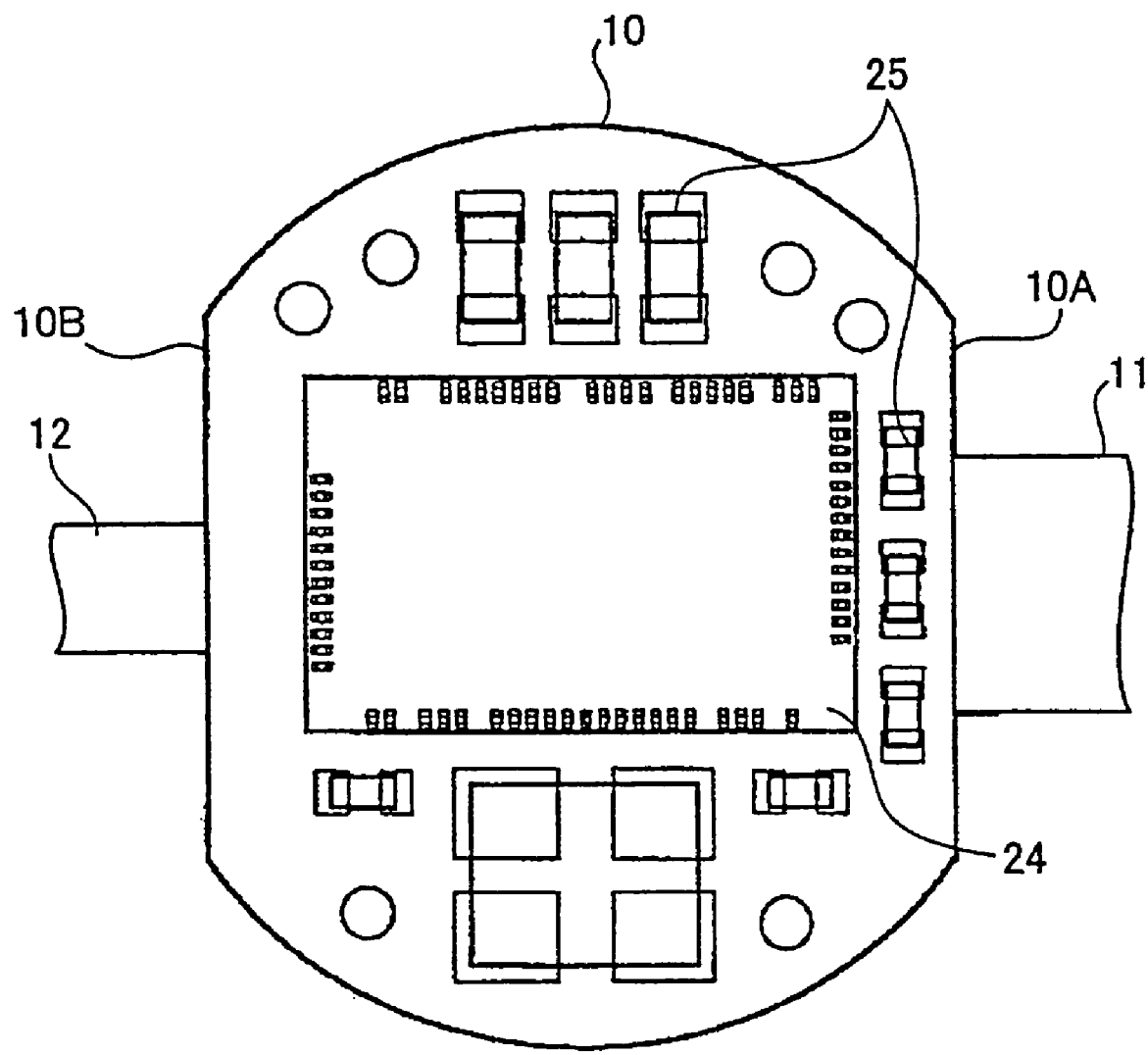
FIG. 6 is a view showing a back surface of the imaging board.
Figure 7:
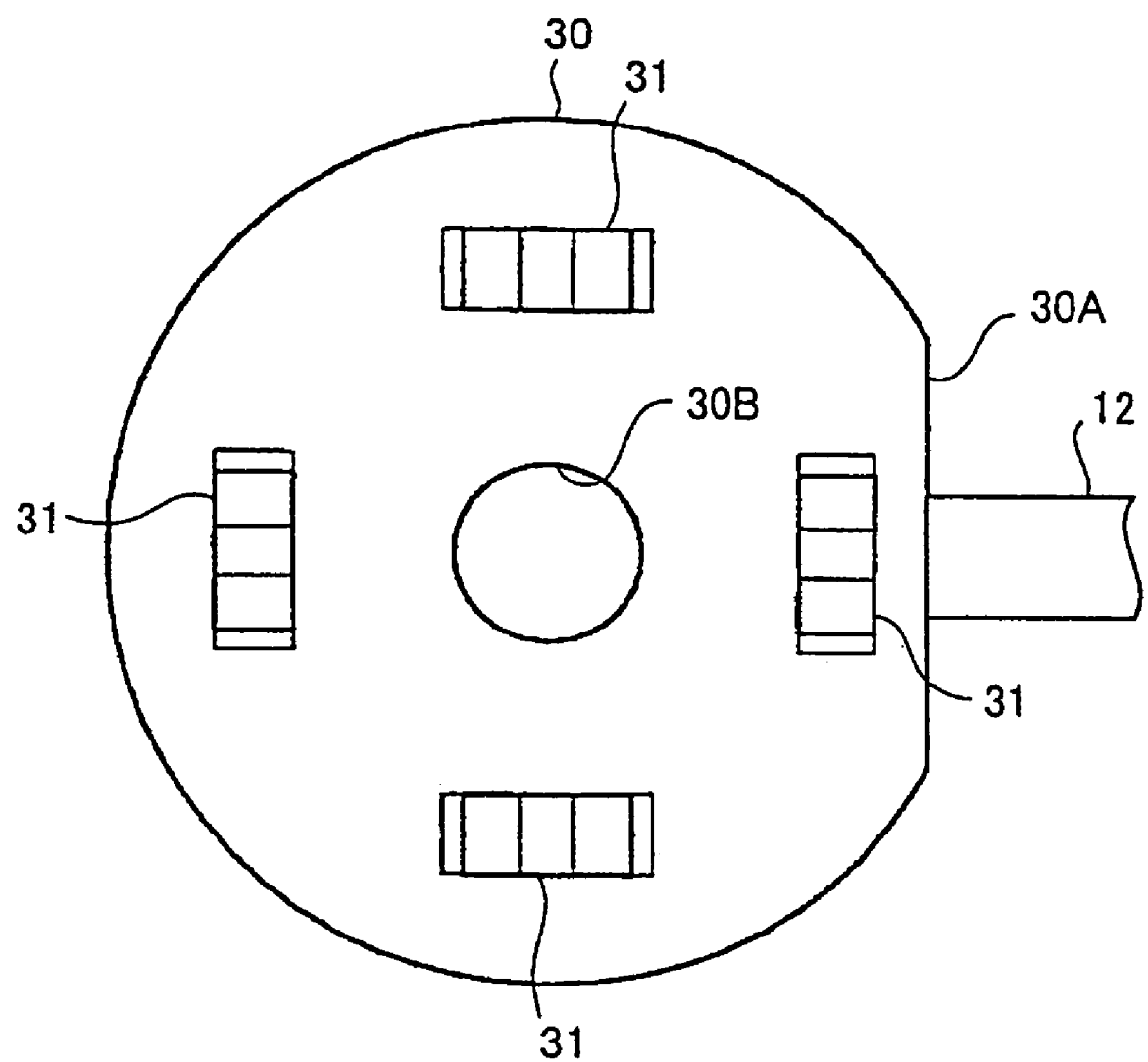
FIG. 7 is a view showing a front surface of an illumination board.
Figure 8:
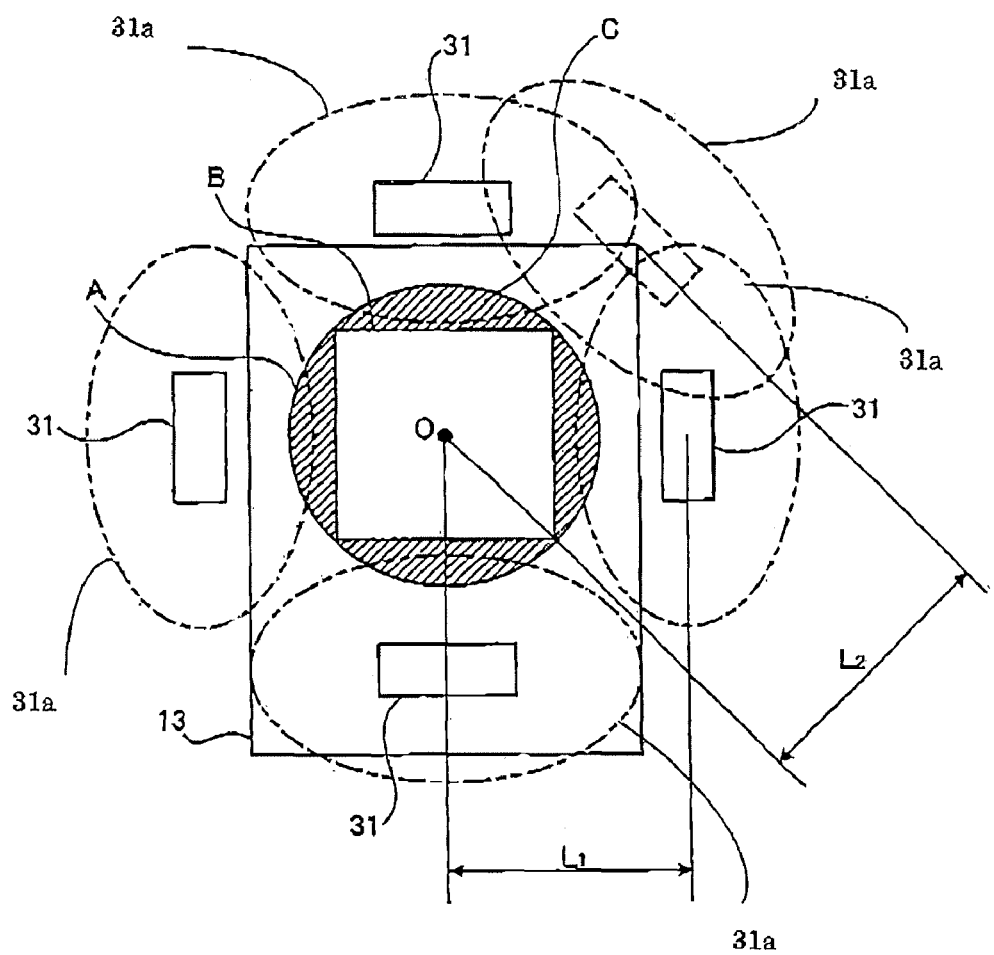
FIG. 8 is a conceptual drawing explaining a positional relationship between illumination components and an image sensor when viewed from an optical axis direction.
Figure 9:
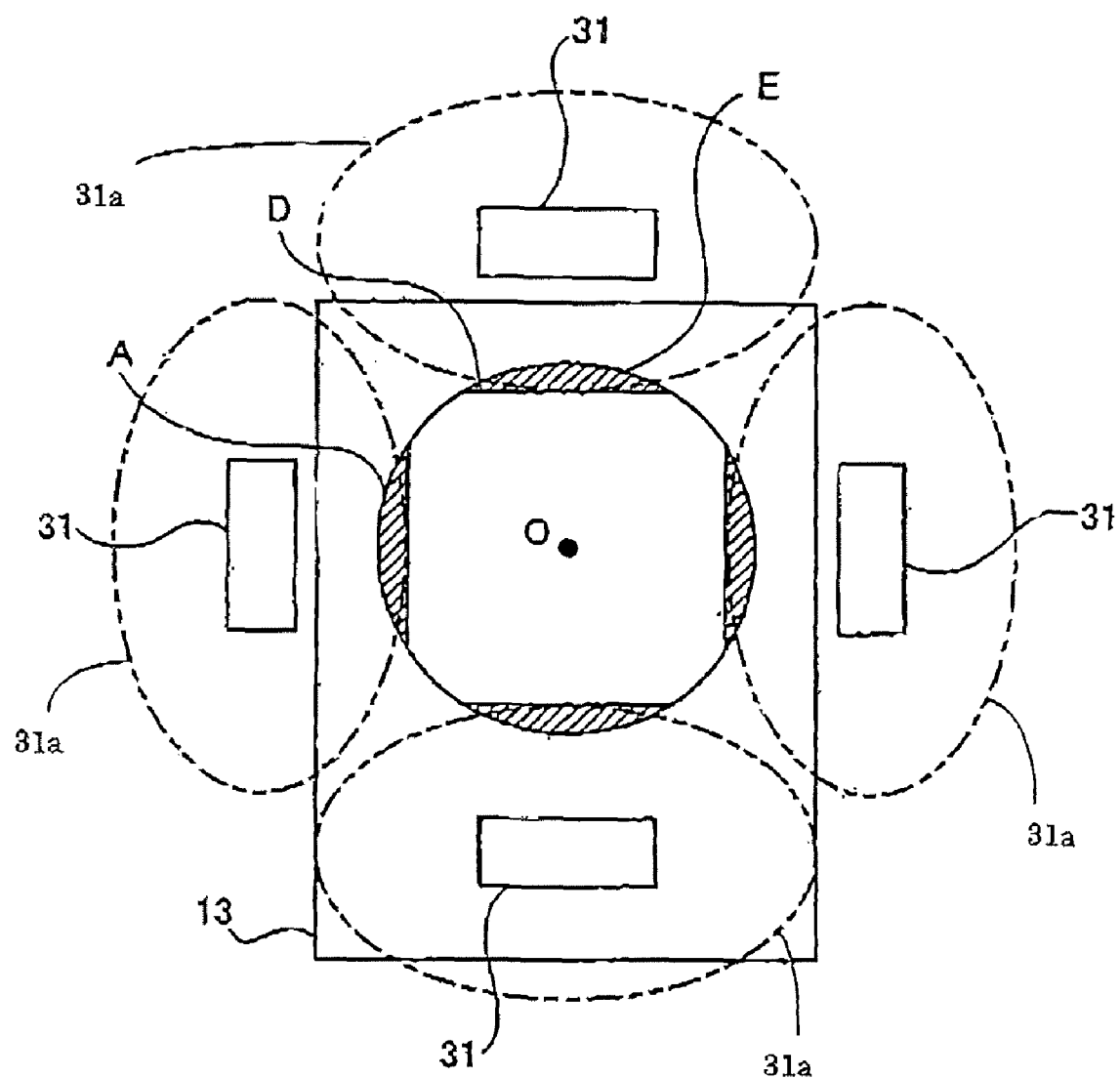
FIG. 9 is a conceptual drawing explaining the positional relationship between the illumination components and the image sensor when viewed from the optical axis direction.
Figure 10:
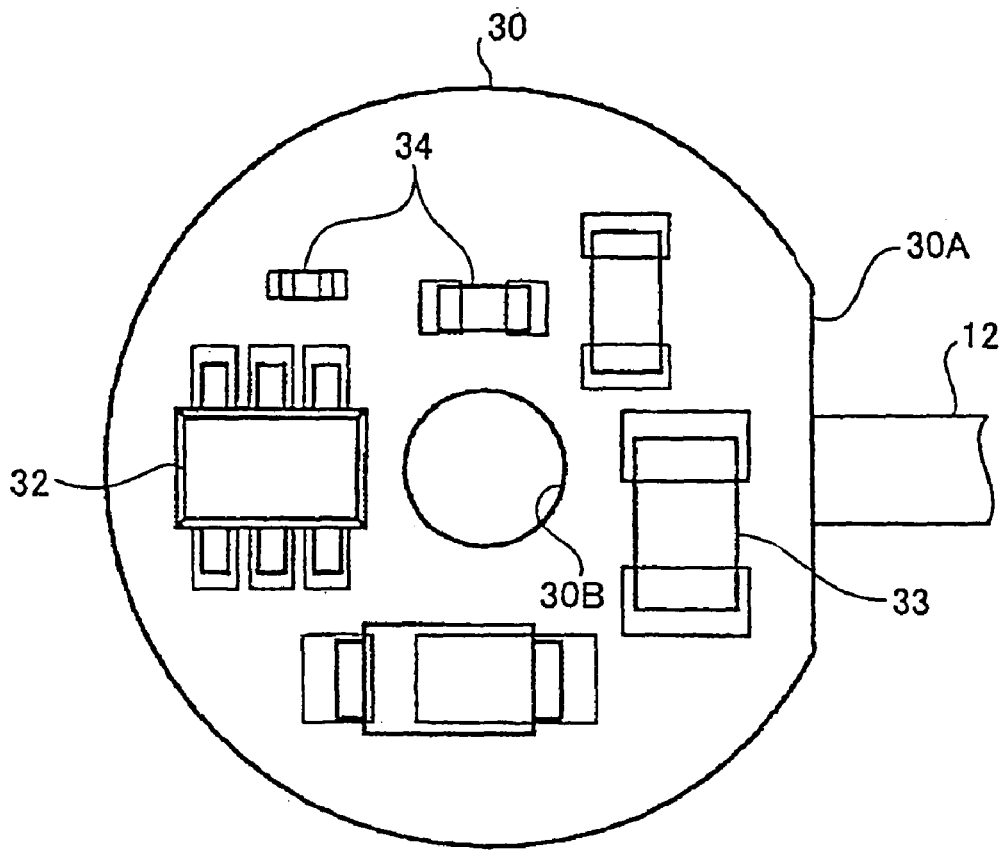
FIG. 10 is a view showing a back surface of the illumination board.
Figure 11:
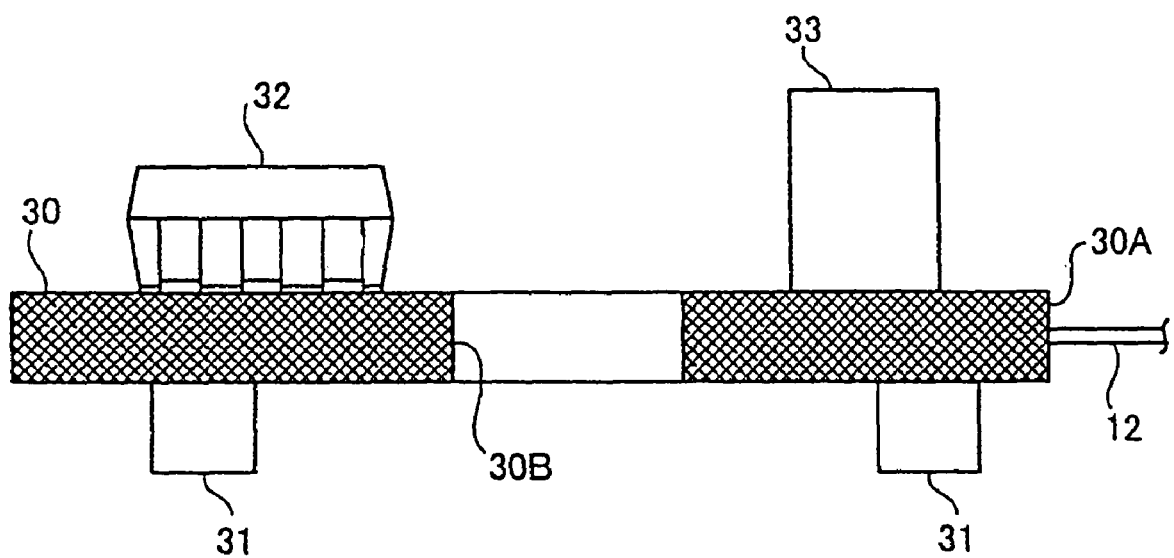
FIG. 11 is a sectional side view showing the illumination board.
Figure 12:
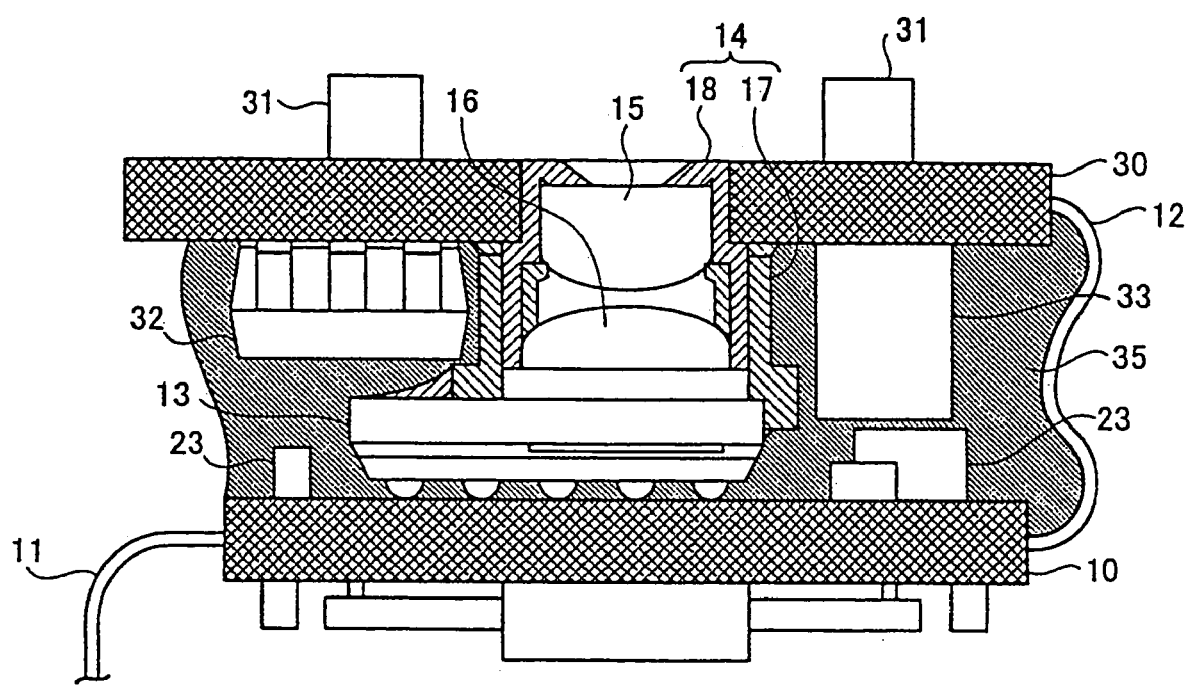
FIG. 12 is a sectional side view showing a state in which the imaging board and the illumination board are placed one on another.
Figure 13:
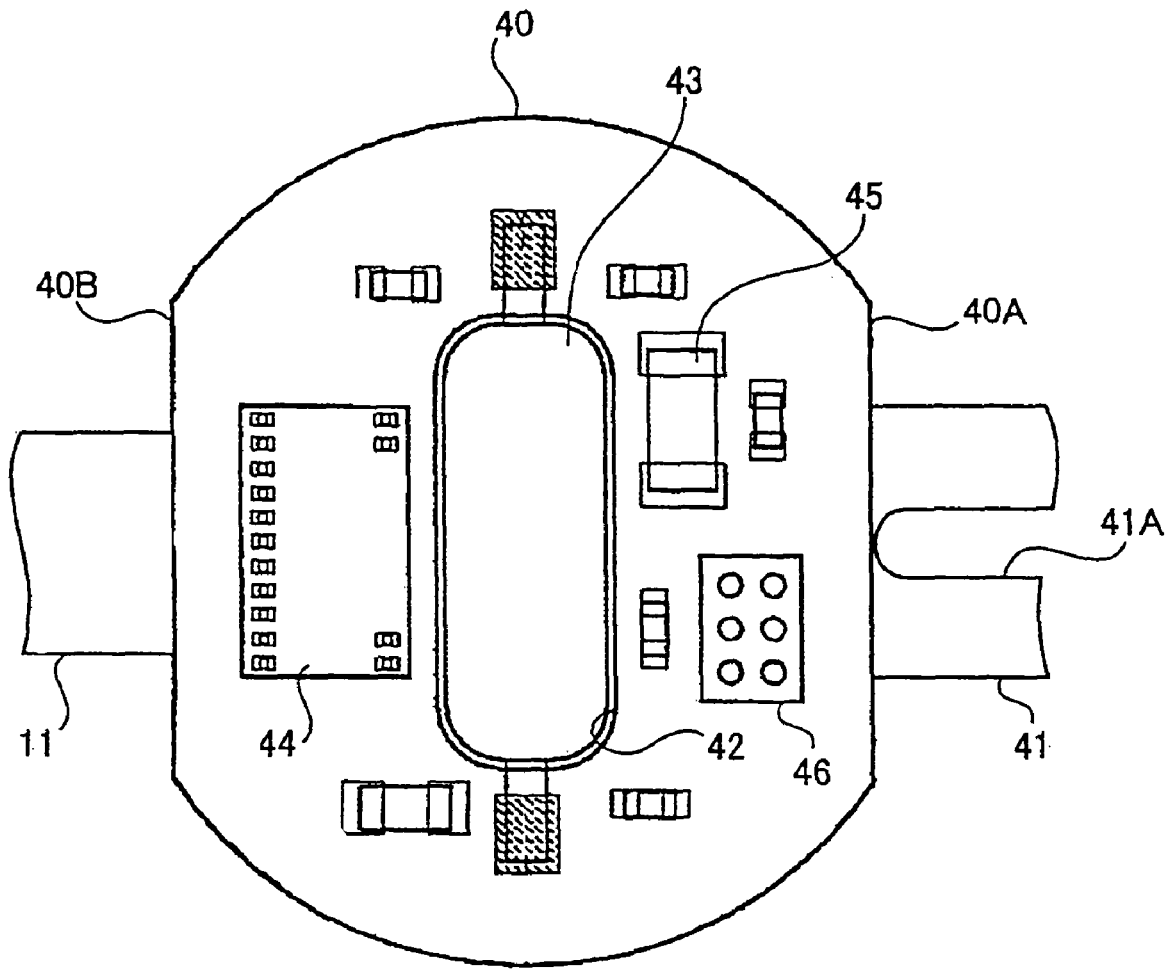
FIG. 13 is a view showing a front surface of a switch board.
Figure 14:
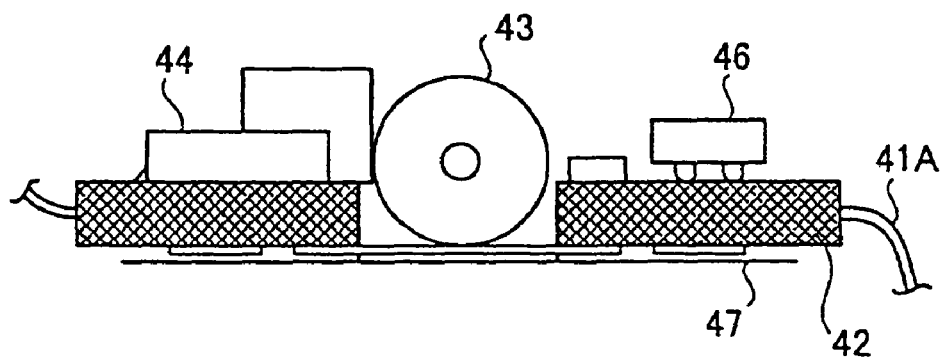
FIG. 14 is a sectional side view showing the switch board.
Figure 15:
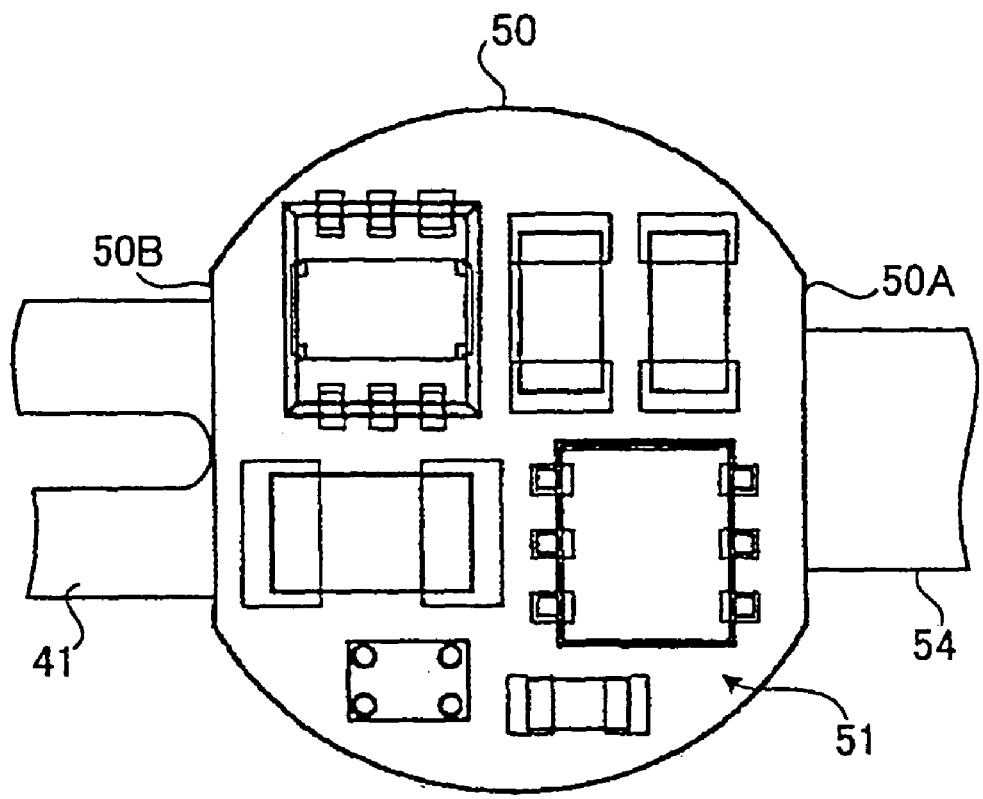
FIG. 15 is a view showing a back surface of a power supply board.
Figure 16:
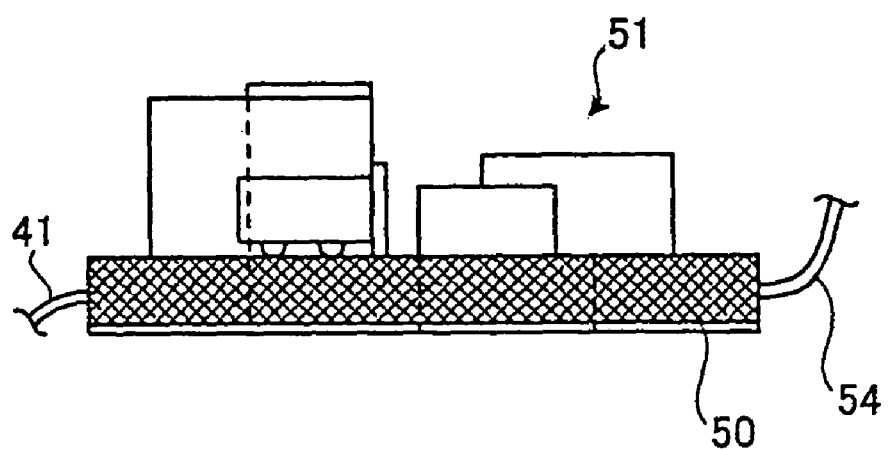
FIG. 16 is a sectional side view showing the power supply board.
Figure 17:
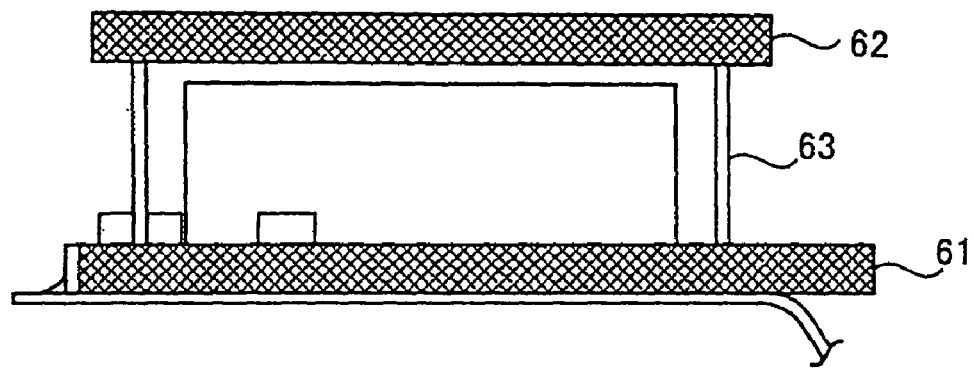
FIG. 17 is a sectional side view showing a transmission unit.
Figure 18:
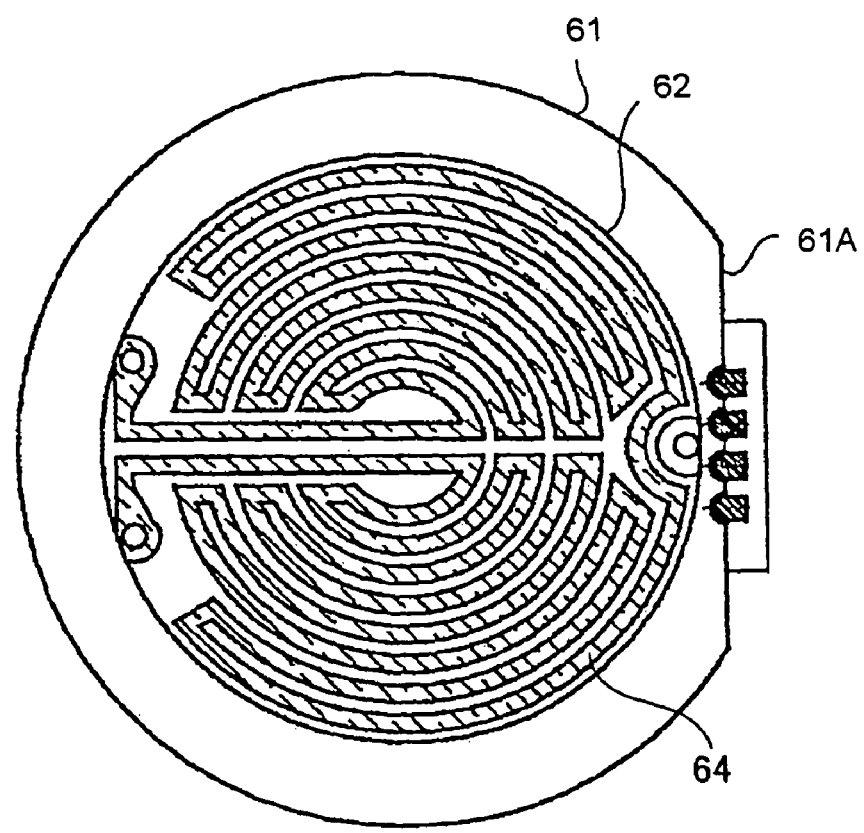
FIG. 18 is a view showing a back surface of the transmission unit.

FIG. 1 is a sectional side view showing a configuration of a capsule-type endoscope according to an embodiment of the invention, FIG. 2 is a top view showing an unfolded form of a rigid/flexible wiring board shown in FIG. 1, FIG. 3 is a bottom view showing the unfolded form of the rigid/flexible wiring board shown in FIG. 1, FIG. 4 is a view showing a front surface of an imaging board, FIG. 5 is a sectional side view showing a state in which a lens attachment member is attached to the imaging board, FIG. 6 is a view showing a back surface of the imaging board, FIG. 7 is a view showing a front surface of an illumination board, FIGS. 8 and 9 are conceptual drawings explaining a positional relationship between illumination components and an image sensor when viewed from an optical axis direction, FIG. 10 is a view showing a back surface of the illumination board, FIG. 11 is a sectional side view showing the illumination board, FIG. 12 is a sectional side view showing a state in which the imaging board and the illumination board are placed one on another, FIG. 13 is a view showing a front surface of a switch board, FIG. 14 is a sectional side view showing the switch board, FIG. 15 is a view showing a back surface of a power supply board, FIG. 16 is a sectional side view showing the power supply board, FIG. 17 is a sectional side view showing a transmission unit, and FIG. 18 is a view showing a back surface of the transmission unit.

The capsule-type endoscope which is introduced from a mouth of a human or an animal into a body cavity to take the images of the body cavity will be described as an example in the embodiment.

As shown in FIG. 1, a capsule-type endoscope 1 includes a folded rigid/flexible board 2 and a capsule 70 which encloses the folded rigid/flexible board 2. As shown in FIGS. 2 and 3, rigid boards 10, 30, 40, and 50 having rigidity and flexible boards 11, 12, 41, and 54 having foldable flexibility are integrally formed in the rigid/flexible board 2. The rigid boards 10, 30, 40, and 50 can be placed one on another by alternately folding the flexible boards 11, 12, and 41 in the opposite directions.

The rigid board includes the imaging board 10, illumination board 30, the switch board 40, and the power supply board 50. The imaging board 10 has a function of imaging the test region in the test subject. The illumination board 30 performs a function of illuminating the test region. The switch board 40 controls supply of electric power for performing each function. The power supply board 50 supplies electric power for performing each function. The illumination board 30 and the imaging board 10, the imaging board 10 and the switch board 40, and the switch board 40 and the power supply board 50 are arranged in parallel respectively. The imaging board 10, the illumination board 30, the switch board 40, and the power supply board 50 are linearly connected by the flexible boards 11, 12, and 41 made of flexible materials. The imaging board 10, the illumination board 30, the switch board 40, and the power supply board 50 are previously integrated with one another. A flexible board 54 is extended from a right-side edge portion 50A of the power supply board 50. A transmission board 61 which constitutes a transmission unit 60 is electrically connected to the flexible board 54 by a through hole land.

As shown in FIG. 4, the imaging board 10 is formed in a substantial disc shape. In a right-side edge portion 10A and a left-side edge portion 10B of the imaging board 10, two sides are formed by linearly cutting out the right-side edge portion 10A and the left-side edge portion 10B in parallel with each other. Flexible boards 11 and 12 are extended from the right-side edge portion 10A and the left-side edge portion 10B respectively. Therefore, in folding the flexible boards 11 and 12, the straight-lined right-side edge portion 10A and left-side edge portion 10B can suppress excessive deformations of the flexible boards 11 and 12.

The right-side edge portion 10A and the left-side edge portion 10B, i.e., the extending directions (two cut-out sides) of the flexible boards 11 and 12 become an arrangement reference of electronic components arranged in the imaging board 10. As shown in FIG. 4, an image sensor 13 is previously arranged in a front surface of the imaging board 10 such that the extending directions of the flexible boards 11 and 12 are aligned with a pixel array direction. More particularly, the image sensor 13, which picks up the images of the test region of the test subject, is mounted on the imaging board 10 by a ball grid array. The image sensor 13 is formed in a polygonal shape, e.g., in a rectangular shape and includes a solid-state imaging device 13A and a rectangular cover glass 13B. An outer circumference of the solid-state imaging device 13A is formed in a rectangular shape having two sets of two parallel sides like CCD (Charge Coupled Diode). The cover glass 13B is longitudinally placed on an upper surface of the solid-state imaging device 13A. The upper surface of the solid-state imaging device 13A is covered by the cover glass 13B. In the embodiment, the pixel array direction is set in parallel with the two sides constituting the outer circumferential shape of the image sensor 13. However, the invention is not limited to the embodiment.

As shown in FIG. 5, a lens support member 14 is attached onto the upper surface of the cover glass 13B which is of the upper surface of the image sensor 13. The lens support member 14 is arranged in close contact to the cover glass 13B. The lens support member 14 supports a small-diameter lens 15 and a large-diameter lens 16. The illumination light emitted from a later-mentioned illumination unit is reflected from the test region, and the small-diameter lens 15 and the large-diameter lens 16 focus the reflected light onto the image sensor 13 in a form of an optical image. The lens support member 14 includes a holder 17 and a lens frame 18.

The holder 17 is formed in a substantially cylindrical shape as a whole, the holder 17 includes a base portion 17A on one end side and a cylindrical portion 17B on the other end side. The base portion 17A abuts against the upper surface (light-receiving surface) of the image sensor 13. The cylindrical portion 17B is extended in an upward direction of the drawing. A hole portion 17C made in the cylindrical portion 17B pierces through the base portion 17A, and the light incident from above the holder 17 can be guided to the image sensor 13. An outer shape of a surface abutting against a lower surface of the base portion 17A, i.e., on the upper surface of the image sensor 13 is formed in substantially square shape having a side substantially equal to a short side of the cover glass 13B. An abutting portion 17D which abuts against a side surface of the cover glass 13B is extended downward from two adjacent sides in the lower edge portion.

In the holder 17, while the lower surface of the base portion 17A abuts against the upper surface of the cover glass 13B, the abutting portion 17D abuts against the two adjacent sides of the upper surface of the cover glass 13B. Therefore, the holder 17 is fixed to the cover glass 13B while previously aligned with the cover glass 13B with high accuracy.

A reinforcement portion 17E having the substantially same shape as the abutting portion 17D is formed while extended from a lower edge portion of the holder 17. The cover glass 13B and the holder 17 are fixed to each other with a black adhesive agent 19 after the alignment. The black adhesive agent 19 is applied to an exposed surface of the cover glass 13B which is not covered with the holder 17, so that the light incident from the exposed surface can be prevented to project the clear image to the image sensor 13. The solid-state imaging device 13A is not limited to CCD. For example, CMOS (Complementary Metal Oxide Semiconductor) may be used as the solid-state imaging device 13A.

A lens frame 18 is attached to the holder 17. The lens frame 18 holds both the small-diameter lens 15 and the large-diameter lens 16 therein. The lens frame 18 is formed in a cylindrical shape, and the lens frame 18 has an outer diameter not larger than an inner diameter of the cylindrical portion 17B of the holder 17. A distal-end portion 18A, a small-diameter portion 18B, and a large-diameter portion 18C are formed in an inner circumferential surface of the lens frame 18. Step portions 18D and 18E are formed in boundary portions respectively.

The distal-end portion 18A takes in the incident light which forms an image on the image sensor 13, and the distal-end side of the distal-end portion 18A is formed in a funnel shape. The small-diameter lens 15 is fitted in the small-diameter portion 18B. In the small-diameter lens 15 having a large refractive index, the front surface is formed in a flat surface, and the back surface is formed in a convex surface. The flat surface portion of the small-diameter lens 15 abuts against the step portion 18D of the distal-end portion 18A, and a circumferential surface portion of the small-diameter lens 15 is fitted in the small-diameter portion 18B. A cylindrical spacer 20 and the large-diameter lens 16 are fitted in the large-diameter portion 18C. In the large-diameter lens 16 having a small refractive index, the front surface is formed in a convex surface, and the back surface is formed in a flat surface. The spacer 20 separates the small-diameter lens 15 from the large-diameter lens 16 at a predetermined interval.

In the outer circumferential surface of the lens frame 18, a small-diameter portion 18F is formed on one end side in the axial direction, a large-diameter portion 18G is formed on the other end side, i.e., on the side of the image sensor 13, and a step portion 18H is formed at a boundary portion. The large-diameter portion 18G is fitted in the inner circumferential surface of the cylindrical portion 17B of the holder 17, and the lens frame 18 can retractably proceed with respect to the holder 17. Therefore, an imaging position where the image is projected to the image sensor 13 can be adjusted by making the lens frame 18 to retractably proceed, and the holder 17 and the lens frame 18 are fixed to each other with an adhesive agent 21 or the like after the imaging position is adjusted. Accordingly, the lens frame 18 and the lenses held therein are aligned in a direction of an optical axis O and fixed to the image sensor 13 via the holder 17.

As shown in FIG. 4, on the front surface of the imaging board 10, large capacitors 22 are arranged on both sides of the image sensor 13 based on the arrangement of the image sensor 13. The large capacitor 22 is an electronic component for a power supply voltage circuit which drives the image sensor 13. The outer circumferential shape of the large capacitor 22 is formed in the substantially rectangular shape having the two sets of the two sides parallel to each other. That is, the large capacitor 22 is arranged such that the two sides of the image sensor 13 are parallel to the two sides of the large capacitor 22. Other electronic components 23, such as a capacitor and a resistor, having predetermined heights are orderly arranged while avoiding the image sensor 13 and large capacitor 22. The electronic components 23 drive the image sensor 13 which is of an electronic component having a predetermined height.

On the other hand, as shown in FIG. 6, in the substantial center of the back surface of the imaging board 10, a microprocessor 24 (Digital Signal Processor) is mounted by flip chip bonding based on the arrangement of the right-side edge portion 10A or the left-side edge portion 10B, i.e., the extending directions of the flexible boards 11 and 12. Electronic components 25 such as a capacitor are orderly arranged based on the microprocessor. Therefore, the electronic components 25 can be integrated, which contributes to the downsizing of the capsule-type endoscope 1. The microprocessor 24 performs drive control of the capsule-type endoscope 1, signal processing of the image sensor 13, and drive control of the illumination board 30.

As shown in FIG. 7, the illumination board 30 is formed in the substantial disc shape, and one side is formed by linearly cutting out a right-side edge portion 30A of the illumination board 30. The right-side edge portion 30A is connected to the flexible board 12 extended from the left-side edge portion of the imaging board 10. Therefore, the excessive deformation of the flexible board 12 can be prevented in folding the flexible board 12.

A through hole 30B which is of a hole piercing through the illumination board 30 is made in a central portion of the illumination board 30. The through hole 30B and the right-side edge portion 30A become the arrangement reference of the electronic components which are arranged in the illumination board 30. The small-diameter portion 18F of the lens frame 18 is fitted in the through hole 30B when the illumination board 30 is placed on the imaging board 10 with a predetermined interval. The through hole 30B has the substantially same shape as the small-diameter portion 18F of the lens frame 18.

Illumination components 31 are arranged on the front surface of the illumination board 30. The illumination component 31 is the illumination units for emitting the illumination light with which the test region of the test subject is illuminated, and the illumination component 31 is one of the illuminating electronic component formed by a light emitting device such as a light emitting diode (Light Emitting Diode) which illuminates the subject in front of the illumination board 30 with the light. The illumination components 31 are arranged at positions corresponding to non-display areas (area where display is not performed in later-mentioned observation screen).

In FIGS. 8 and 9, for a later-mentioned display area and non-display areas in the light-receiving surface of the image sensor 13, an arrangement relationship between the illumination components 31 and the image sensor 13 when viewed from the direction of the optical axis O is described on the same plane by projecting arrangement positions of the illumination components 31 to the direction of the optical axis O. The arrangement relationship between the illumination components 31 and the image sensor 13 will be described in detail with reference to FIGS. 8 and 9. As shown in FIG. 8, an image A obtained by the image sensor 13 has a circular shape. In the circular image A, assuming that a square area is a display area B in the observation screen, the hatched residual area becomes a non-display area C in the observation screen. Because the non-display area C is not displayed on the observation screen, a clear image is not required in the non-display area C. Even if the light from the illumination components 31 has an influence (shown schematically by alternate long and two short-dashed lines 31a) on the non-display area C, the non-display area C is not displayed on the observation screen. Accordingly, the illumination components 31 are arranged close to the display area B, and the illumination components 31 are arranged at the positions corresponding to the non-display areas C, i.e., within a range where the light from the illumination components 31 has no influence on the image of the display area B.

As shown in FIG. 9, assuming that an octagonal area where corner portions of the square are cut down is a display area D, the hatched residual area becomes a non-display area E in the observation screen. Because the non-display area E is also not displayed on the observation screen, a clear image is not required in the non-display area E. Even if the light from the illumination components 31 has an influence (shown schematically by alternate long and two short-dashed lines 31a) on the non-display area E, the non-display area E is not displayed on the observation screen. Accordingly, the illumination components 31 are arranged close to the display area D, and the illumination components 31 are arranged at the positions corresponding to the non-display areas E, i.e., within a range where the light from the illumination components 31 has no influence on the image of the display area D.

In other words, in both the cases of FIGS. 8 and 9, the image sensor 13 has a light-receiving surface including an effective area (namely, display area on the aforementioned observation screen) and an ineffective area (namely, non-display area on the aforementioned observation screen). In the effective area, the image sensor 13 receives the illumination light reflected from the test region, and the image sensor 13 generates the image of the test region. The ineffective area does not contribute to the image generation. An area on the illumination board 30 is defined as a component arrangement unit. The area on the illumination board 30 is obtained by projecting the ineffective area of the light-receiving surface onto the illumination board 30 along the optical axis O which is the direction orthogonal to the light-receiving surface of the image sensor 13. The illumination components 31 which are of an example of the illuminating electronic component are arranged in the component arrangement unit.

As shown in FIG. 1, because a predetermined visual field range based on a predetermined view angle α is formed by the lenses (small-diameter lens 15 and large-diameter lens 16) which are supported by the lens frame 18, it is also necessary to arrange the illuminating electronic component in consideration of the view angle α. That is, from the viewpoint of length in a lengthwise direction, the illumination components 31 which are of the illuminating electronic component are arranged out of the visual field range which is formed by the lenses. The illuminating electronic component is not limited to the illumination component 31, but the illuminating electronic component may include an electronic component for driving the illumination component 31.

When the illumination components 31 are arranged in the above-described manner, a distance between the optical axis O and the illumination components 31 can be shortened ($L_1$ for $L_2$) as compared with the case (shown schematically by alternate long and two short-dashed lines 31a in FIG. 8) where the illumination components 31 are arranged so as not to have an influence on the obtained image irrespective of the display areas B and D and non-display areas C and E. Therefore, the capsule-type endoscope can be downsized in the radial direction. The illumination components 31 are not limited to the light emitting diode. For example, EL (electroluminescence) may be used as the illumination components 31. The number of the illumination components 31 is not limited to four.

As shown in FIGS. 10 and 11, a driving electronic component 32, an electronic component 33, and electronic components 34 such as a small capacitor are arranged on the back surface of the illumination board 30. The driving electronic component 32 drives the illumination components 31. The electronic component 33 stably supplies the voltage to the illumination components 31.

As shown in FIG. 12, in the case where the imaging board 10 and the illumination board 30 are placed one on another with a predetermined interval by folding the flexible board 12 connecting the imaging board 10 and the illumination board 30, the tall electronic components such as the driving electronic component 32 and the electronic component 33 for stably supplying the voltage face the low-profile electronic components 23, such as the capacitor and the resistor, which are arranged on the surface (front surface of imaging board 10) facing the illumination board 30 of the imaging board 10.

On the other hand, in the case where the imaging board 10 and the illumination board 30 are placed one on another by folding the flexible board 12 connecting the imaging board 10 and the illumination board 30, the low-profile electronic components 34 such as a small capacitor face the tall and large capacitor 22 which is arranged on the surface (front surface of imaging board 10) facing the illumination board 30 of the imaging board 10.

That is, in the rigid/flexible board 2 in which the imaging board 10 and the illumination board 30 are arranged by folding the flexible board 12 connecting the imaging board 10 and the illumination board 30, the tall driving electronic component 32, the electronic component 33 for stably supplying the voltage, the low-profile electronic components 34 such as the small capacitor are arranged in the back surface of the illumination board 30, while the tall and large capacitor 22 arranged on the front surface of the imaging board 10, the low-profile small capacitor, and the electronic components 25 such as the resistor are alternately combined.

Therefore, an interval between the imaging board 10 and the illumination board 30 can be made narrower than a sum of a height of the tall electronic component arranged on the front surface of the imaging board 10 and the tall electronic component arranged on the back surface of the illumination board 30. The flexible board 12 is formed to be longer than the assembled length of the image sensor 13 and the lens support member 14.

After the illumination board 30 having the above configuration is arranged while facing the imaging board 10 with a predetermined interval, the illumination board 30 and the imaging board 10 are fixed to each other while electrically insulated using an adhesive agent 35 having an insulating property.

As shown in FIGS. 13 and 14, similarly to the imaging board 10, the switch board 40 is formed in the substantial disc shape, and a right-side edge portion 40A and a left-side edge portion 40B of the switch board 40 are cut down by parallel two sides. The left-side edge portion 40B is connected to the flexible board 11 extended from the right-side edge portion of the imaging board 10, and the flexible board 41 is extended from the right-side edge portion 40A. Therefore, the excessive deformation of the flexible board 41 can be suppressed in folding the flexible board 41.

The right-side edge portion 40A and the left-side edge portion 40B, i.e., the extending directions of the flexible boards 11 and 41 become the arrangement reference of the electronic components arranged in the switch board 40. In the central portion of the switch board 40, an elliptical hole portion 42 is made in parallel with the two sides of the right-side edge portion 40A and the left-side edge portion 40B.

A reed switch 43 is arranged on the front surface of the switch board 40 so as to sink into the hole portion 42, which allows a protrusion height of the reed switch 43 to be suppressed on the front surface side of the imaging board 10. The reed switch 43 is a latch type switch. The reed switch 43 is turned off in the initial state, and the reed switch 43 is turned on by distancing a magnet (not shown) located close to the reed switch 43. The electronic components such as a memory 44, an oscillator 45, and MIX 46 are orderly arranged around the reed switch 43.

Initial values of the microprocessor 24, white balance and variations in color of the solid-state imaging device 13A, a device-specific number of the capsule-type endoscope 1, and the like are stored in the memory 44. The oscillator 45 supplies a basic clock to the microprocessor 24. The MIX 46 is mounted by the flip chip bonding. When an image signal and a clock signal, which are outputted from the microprocessor 24, are transmitted, the MIX 46 serves to mix the image signal and the clock signal into one signal. As shown in FIG. 1, a contact 47 abutting against a positive electrode of a battery is provided on the back surface of the switch board 40. The contact 47 is formed with a plate spring.

As shown in FIGS. 15 and 16, the power supply board 50 is formed in the substantial disc shape, and a right-side edge portion 50A and a left-side edge portion 50B of the power supply board 50 are cut down by parallel two sides. The left-side edge portion 50B is connected to the flexible board 41 extended from the right-side edge portion 40A of the switch board 40. Therefore, the deformation of the flexible board can be suppressed in folding the flexible board. A contact (not shown) abutting against a negative electrode of the battery is provided on the front surface of the power supply board 50, and a DC-DC converter 51 is provided in the back surface of the power supply board 50. The DC-DC converter 51 controls the voltage obtained by the battery in order to obtain the constant voltage necessary for the capsule-type endoscope 1.

As shown in FIG. 1, plural (three in the embodiment) batteries 52 are sandwiched between the power supply board 50 and the switch board 40, and the plural batteries 52 are integrated while gripped between the switch board 40 and the power supply board 50 by shrinking a cross-sectional heat-shrinkable tubing 53. An elliptical slit 41A is formed in the central portion of the flexible board 41, and the flexible board 41 is in close contact with the batteries 52 along the outer circumferences of the batteries 52. A button-shaped silver oxide battery whose outer shape is a disc forms the battery 52. The plural batteries 52 are connected in series, and the batteries 52 are arranged such that the negative electrode side is orientated toward the power supply board 50. The battery 52 is not limited to the silver oxide battery. For example, a rechargeable battery and a generating type battery may also be used.

The flexible board 54 is extended to the right-side edge portion 50A of the power supply board 50, and a transmission unit 60 is connected to the flexible board 54. The transmission unit 60 is formed independently of the rigid/flexible board 2, and then the transmission unit 60 is connected to the flexible board 54 by the through hole land.

As shown in FIGS. 17 and 18, the transmission unit 60 includes a transmission board 61 and an antenna board 62. The transmission board 61 is formed in the disc shape. A right-side edge portion 61A of the transmission board 61 is formed by linearly cutting out the transmission board 61. The right-side edge portion 61A becomes the arrangement reference of the electronic components arranged in the transmission board 61, and the electronic components are arranged in the back surface of the transmission board 61 based on the right-side edge portion 61A. The antenna board 62 is attached to a terminal 63 vertically provided from the back surface of the transmission board 61, and a substantially spiral antenna pattern 64 is formed in the back surface of the antenna board 62. The transmission unit 60 can take out the signal having predetermined frequency, amplitude, and waveform from the signal to which the mixing is already performed by the switch board 40, and the transmission unit 60 can transmit the picked up signal to the outside from the antenna board 62.

As shown in FIG. 1, after the switch board 40 and the imaging board 10, and the power supply board 50 and transmission unit 60 are arranged with a predetermined interval while facing each other respectively, the switch board 40 and imaging board 10, and the power supply board 50 and transmission unit 60 are fixed while electrically insulated by the adhesive agent 65 having the insulating property.

The laminated rigid/flexible board 2 constitutes the inside of the capsule-type endoscope 1, and the laminated rigid/flexible board 2 is enclosed by a capsule 70. The capsule 70 includes a distal-end cover 71 and a case 72.

The distal-end cover 71 is formed in a hemispherical dome shape, and the rear side of the distal-end cover 71 is opened. The front surface side of the illumination board 30 is covered with the distal-end cover 71. The distal-end cover 71 has transparency or translucency. The illumination light emitted from the illumination components 31 is transmitted through the distal-end cover 71 to the outside of the capsule 70, and the image illuminated with the illumination light is also transmitted through the distal-end cover 71 to the inside of the capsule 70.

A connection end portion 71A is formed over the circumference of the opened portion of the distal-end cover 71. The connection end portion 71A is extended toward the opened direction (toward rear side). The connection end portion 71A has a cylindrical shape in which a draft angle does not exist in molding. The outer circumferential surface of the connection end portion 71A constitutes a connection surface with the case 72, and an endless protrusion 71B is provided over the circumference of the connection surface. In an overlapping width of the connection surface, the protrusion 71B is provided at an arbitrary position, where the protrusion 71B is separated away from the edge of the connection end portion 71A of the distal-end cover 71, e.g., at the central portion in the overlapping width direction.

As shown in FIG. 1, in the distal-end cover 71, the base end portion from which the connection end portion 71A is extended has a thick portion 71C. In the thick portion 71C, a cross section is formed thicker than that of the connection end portion 71A or the hemispherical dome shape portion with which the front surface side of the illumination board 30 is covered. The thick portion 71C secures strength in the connection end portion 71A of the distal-end cover 71. For example, the thick portion 71C prevents a crack of the distal-end cover 71 in the case of accidental dropping.

In the distal-end cover 71, an abutting portion 71D is formed in the inner circumferential surface of the base end portion from which the connection end portion 71A is extended. The distal-end cover 71 and the folded rigid/flexible board 2 can be positioned at a predetermined positional relationship in the axial direction by causing the illumination board 30 to abut against the abutting portion 71D.

In the distal-end cover 71, an inner diameter of the base end portion from which the connection end portion 71A is extended is substantially equal to outer diameters of the illumination board 30 and imaging board 10. Therefore, the distal-end cover 71 and the folded rigid/flexible board 2 can be positioned in the radial direction, the inner circumferential surface of the connection end portion 71A in the distal-end cover 71 abuts against the outer circumferential surface of the illumination board 30, and the connection end portion 71A regulates the inward deformation of the capsule 70.

In the case where the folded rigid/flexible board 2 is accommodated inside the capsule 70 by connecting the distal-end cover 71 and the case 72, the distal-end cover 71 and the case 72 are fixed by injecting the adhesive agent between the inner circumferential surface of the connection end portion 71A in the distal-end cover 71 and the folded rigid/flexible board 2. Thus, when the folded rigid/flexible board 2 is fixed to the distal-end cover 71, the illumination board 30 of the rigid/flexible board 2 is positioned in the distal-end cover 71.

The case 72 is a portion with which the folded rigid/flexible board 2 is covered on the rear side of the distal-end cover 71. In the case 72, a cylindrical drum portion 72A and a rear-end portion 72B having a substantially hemispherical dome shape are integrally formed, and the front side of the drum portion 72A is opened. A connection end portion 72D is formed over the circumference of an opening 72C of the case 72. The connection end portion 72D is extended toward the opened direction (toward front side). The connection end portion 72D has the cylindrical shape in which the draft angle does not exist in molding. The inner circumferential surface of the connection end portion 72D constitutes the connection surface with the distal-end cover 71, and an endless groove 72E is provided over the circumference of the connection surface. The groove 72E is provided according to the position where the protrusion 71B is provided in the distal-end cover 71. The overlapping width ranges from about 1 to about 5 mm, and preferably 3 mm. The groove 72E is preferably provided in the central portion of the overlapping width.

The protrusion 71B and groove 72E engage with each other when the distal-end cover 71 and the case 72 overlap each other in the connection surface. Thus, the engagement between the protrusion 71B and the groove 72E holds the state in which the distal-end cover 71 and the case 72 are connected to each other. Because the protrusion 71B is provided over the circumference of the connection surface while the groove 72E is provided over the circumference of the connection surface, the protrusion 71B and groove 72E engage with each other to connect the distal-end cover 71 and the case 72, which allows each connection surface to be relatively slid and rotated.

A resin material 80 is applied to the outer circumferential surface of the folded rigid/flexible board 2, and the adhesive agent is applied to the connection surface of the connection end portion of the distal-end cover 71. Then, the distal-end cover 71 and the case 72 are connected by overlapping the connection surface of the connection end portion of the distal-end cover 71 and the connection surface of the connection end portion of the case 72. Therefore, the gap between the outer circumferential surface of the folded rigid/flexible board 2 and the inner circumferential surface of the capsule is filled with the resin material, and the adhesive agent intrudes between the connection surface of the connection end portion of the distal-end cover 71 and the connection surface of the connection end portion of the case 72. Then, the distal-end cover 71 and the case 72 are relatively slid and rotated while connected to each other, which allows the adhesive agent to spread into between the connection surface of the connection end portion of the distal-end cover 71 and the connection surface of the connection end portion of the case 72. As a result, watertightness is secured between the distal-end cover 71 and the case 72, and the whole of the capsule 70 can be sealed in the water-tight manner.

As shown in FIG. 1, chamfering is performed to the connection portions of the distal-end cover 71 and the case 72, which emerge on the outer surface of the capsule in the state in which the distal-end cover 71 and the case 72 are connected. The chamfering decreases a step which might be generated in the outer surface of the capsule between the distal-end cover 71 and the case 72. Therefore, the case in which something is caught in the step to generate external force separating the distal-end cover 71 and the case 72 can be prevented.

The distal-end cover 71 is made of a cycloolefin polymer, polycarbonate, acryl, polysulfone, or urethane. Particularly, the cycloolefin polymer or polycarbonate can preferably be used in order to secure optical performances and strength of the distal-end cover 71. The case 72 is made of a cycloolefin polymer, polycarbonate, acryl, polysulfone, or urethane. Particularly, polycarbonate can preferably be used in order to secure the strength of the case 72.

Figure 19:
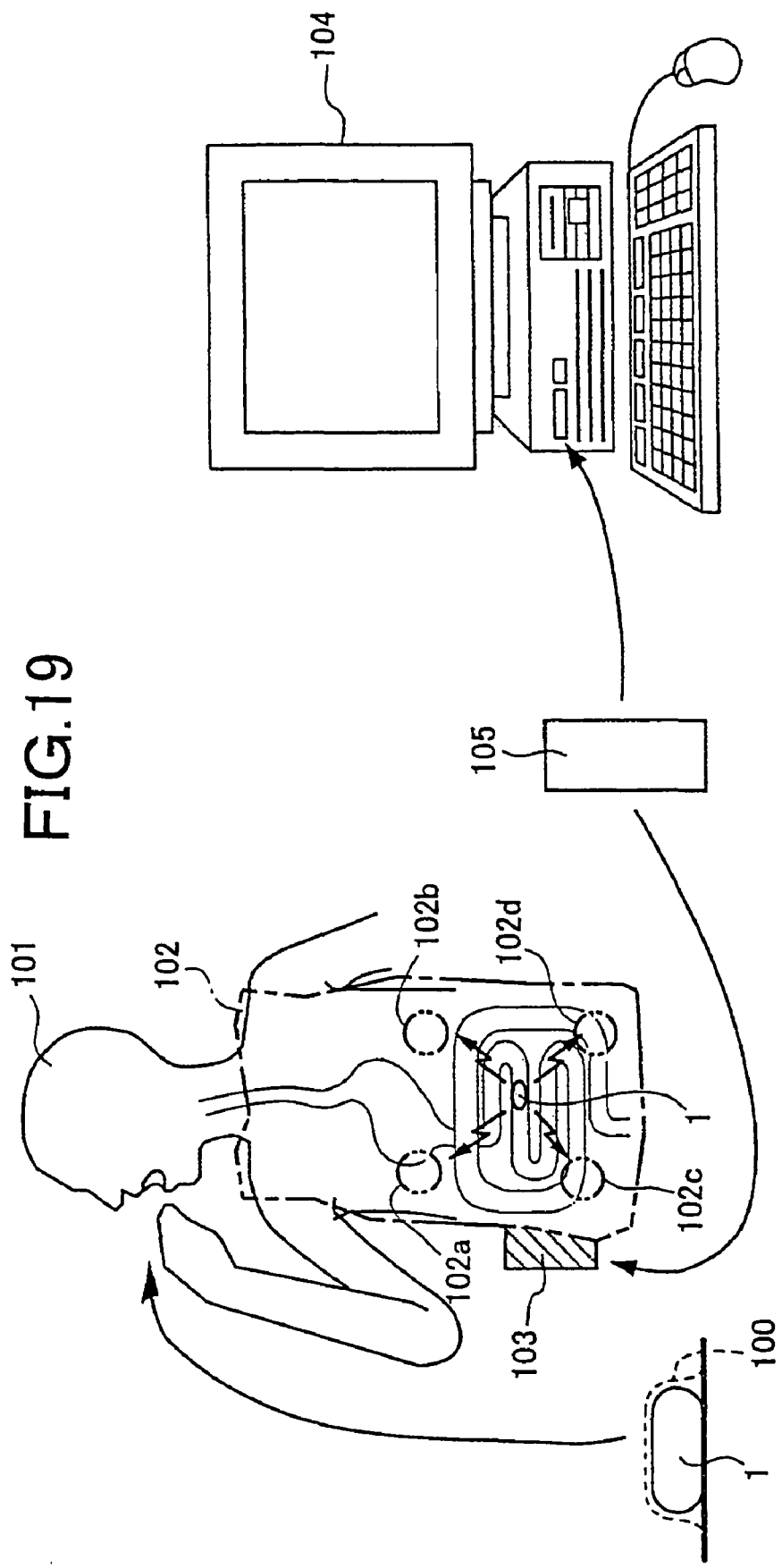
FIG. 19 is a schematic view showing a medical system in which the capsule-type endoscope is used.

Then, a medical system in which the above described capsule-type endoscope is used will be described. FIG. 19 is a schematic view showing the medical system in which the capsule-type endoscope is used.

As shown in FIG. 19, the medical system in which the capsule-type endoscope is used includes the capsule-type endoscope 1 stored in a package 100, a jacket 102 which a patient, i.e., a subject 101 wears, a receiver 103 which is detachably attached to the jacket 102, and a computer 104.

Antennas 102a, 102b, 102c, and 102d which pick up radio waves transmitted from the antenna board 62 of the capsule-type endoscope 1 are provided in the jacket 102, and the capsule-type endoscope 1 can communicate with a receiver 103 through the antennas 102a to 102d. The number of antennas is not limited to the four antennas 102a to 102d shown in FIG. 17 as long as the plural antennas are used. The radio wave can be well received at a position depending on the movement of the capsule-type endoscope 1 by the antennas 102a to 102d. The position of the capsule-type endoscope 1 in the body cavity can also be detected from the received intensity of each of the antennas 102a to 102d.

The receiver 103 performs the white balance process to the taken image data sequentially received, and the image data to which the white balance process is already performed is stored in a CompactFlash (registered trademark) memory card (CF memory card) 105. The radio wave reception by the receiver 103 is not synchronized with the start of image pickup by the capsule-type endoscope 1, but the start and the end of the ratio wave reception are controlled by an operation of an input unit of the receiver 103.

The computer 104 reads from and writes to the CF memory card 105. In the computer 104, a doctor or a nurse (examiner) performs image processing to the images of the organs or the like in the patient body, i.e., the test subject, taken by the capsule-type endoscope 1, to display the images on an observation screen (monitor). The observation screen has a square shape or an octagonal shape in which the four corners of the square are cut down.

A schematic operation of the medical system will be described below. Before diagnostic examination is started, the capsule-type endoscope 1 is taken out from the package 100. By doing this, the reed switch 43 of the capsule-type endoscope 1 is transferred from the OFF state to the ON state to turn on the main power supply. Then, the subject swallows the capsule-type endoscope 1 from the mouth. Therefore, the capsule-type endoscope 1 passes through the gullet and progresses through the body cavity by vermicular movements of alimentary canals. The capsule-type endoscope 1 sequentially picks up the images in the body cavity. The capsule-type endoscope 1 outputs the radio waves of the taken image sequentially or as needed. The antennas 102a to 102d of the jacket 102 pick up the radio waves. The radio waves picked up by the antennas 102a to 102d are transmitted to the receiver 103 in the form of the signal. When the observation (diagnostic examination) of the subject 101 by the capsule-type endoscope 1 is completed, the CF memory card 105 in which the taken image data is stored is taken out from the receiver 103, and the CF memory card 105 is inserted into a memory card insertion hole of the computer 104. In the computer 104, the taken image data stored in the CF memory card 105 is read and stored according to the individual patient. In making the diagnosis, the taken image is processed to display the image on the monitor of the computer 104.

In the capsule-type endoscope 1 of the above embodiment, the illumination board 30, the imaging board 10, the switch board 40, and the power supply board 50 are linearly connected in this order by the flexible boards 11, 12, and 41. However, the illumination board 30, the imaging board 10, the switch board 40, and the power supply board 50 may be connected not in a linear manner as far as they are placed in this order when the flexible boards 11, 12, and 41 are folded. For example, the illumination board 30, the imaging board 10, the switch board 40, and the power supply board 50 may not always be formed in the straight line as long as the illumination board 30, the imaging board 10, the switch board 40, and the power supply board 50 are located in the same plane.

Thus, the capsule-type endoscope 1 of the embodiment includes the illumination board 30 which is prepared to mount the illuminating electronic components, the illuminating electronic component being necessary to illuminate the test region of the test subject with illumination light; the image sensor 13 which has the light-receiving surface including the effective area (display areas B and D) and the ineffective area (non-display areas C and E), the illumination light reflected from the test region being received to generate the image of the test region in the effective area, the ineffective area not contributing to the image generation; the imaging board 10 which is arranged in parallel with the illumination board 30, the image sensor 13 being mounted on the imaging board 10; and the component arrangement unit in which the illuminating electronic components are arranged, the illuminating electronic components being provided in an area on the illumination board 30, the area on the illumination board 30 being obtained by projecting the ineffective area (non-display areas C and E) in the light-receiving surface of the image sensor 13 to a direction orthogonal to the light-receiving surface of the image sensor. Therefore, the capsule-type endoscope of the present invention can be smaller than the conventional one while maintaining the conventionally required basic functions, and the subject can easily swallow the capsule-type endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule-type endoscope comprising:
an illumination board which is prepared to mount an illuminating electronic component necessary to illuminate a test region of a test subject with illumination light;
an image sensor which has a light-receiving surface including an effective area and an ineffective area, the illumination light reflected from the test region being received to generate an image of the test region in the effective area, the ineffective area not contributing to the image generation;
an imaging board which is arranged in parallel with the illumination board, the image sensor being mounted on the imaging board; and
a component arrangement unit in which the illuminating electronic component is arranged, the illuminating electronic component being provided in an area on the illumination board, the area on the illumination board being arranged close to the effective area and at a position corresponding to the ineffective area within a range where the illumination light from the illumination electronic component has no influence on the image of the effective area;
wherein in the case where the imaging board and the illumination board are arranged in the capsule by folding the flexible board connecting the imaging board and the illumination board, a tall electronic component disposed on a front surface of the imaging board faces a small-profile electronic component disposed on a back surface of the illumination board and a small-profile electronic component disposed on the front surface of the imaging board faces a tall electronic component disposed on the back surface of the illumination board.

2. The capsule-type endoscope according to claim 1, further comprising
a lens which forms a visual field range based on a predetermined view angle, the lens focusing the illumination light reflected from the test region onto the light-receiving surface in a form of an optical image of the test region,
wherein the illuminating electronic component is arranged in the component arrangement unit so as to be arranged out of the visual field range formed by the lens.

3. The capsule-type endoscope according to claim 2, wherein the illuminating electronic component includes a light emitting device which emits the illumination light, the test region of the test subject being illuminated with the illumination light.

4. The capsule-type endoscope according to claim 1, wherein the illuminating electronic component includes a light emitting device which emits the illumination light, the test region of the test subject being illuminated with the illumination light.

* * * * *